United States Patent
Mikami (10) Patent No.: US 10,416,438 B2
(45) Date of Patent: Sep. 17, 2019

(54) IMAGING DEVICE FOR IMAGING INSIDE OF SUBJECT AND ENDOSCOPE DEVICE USING THE SAME

(71) Applicant: OLYMPUS CORPORATION, Tokyo (JP)

(72) Inventor: Masato Mikami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 92 days.

(21) Appl. No.: 15/252,462

(22) Filed: Aug. 31, 2016

(65) Prior Publication Data

US 2016/0370572 A1      Dec. 22, 2016

Related U.S. Application Data

(63) Continuation of application No. PCT/JP2015/054152, filed on Feb. 16, 2015.

(30) Foreign Application Priority Data

Mar. 3, 2014   (JP) .................................. 2014-040992

(51) Int. Cl.
*A61B 1/05*           (2006.01)
*G02B 23/24*          (2006.01)
(Continued)

(52) U.S. Cl.
CPC ........ *G02B 23/2484* (2013.01); *A61B 1/0011* (2013.01); *A61B 1/00096* (2013.01);
(Continued)

(58) Field of Classification Search
CPC ... A61B 1/00096; A61B 1/00163; A61B 1/05; A61B 1/051; G02B 23/2423;
(Continued)

(56) References Cited

U.S. PATENT DOCUMENTS 4,643,170 A * 2/1987 Miyazaki ................. A61B 1/05
                                                      348/65
4,682,219 A * 7/1987 Arakawa ................. A61B 1/05
                                                      348/76
(Continued)

FOREIGN PATENT DOCUMENTS

JP     S63-124495 A     5/1988
JP     2000-271066 A    10/2000
(Continued)

OTHER PUBLICATIONS

Chinese Office Action dated Aug. 1, 2017 in Chinese Patent Application No. 201580011280.9.
(Continued)

*Primary Examiner* — John P Leubecker
(74) *Attorney, Agent, or Firm* — Scully, Scott, Murphy & Presser, P.C.

(57) ABSTRACT

An imaging device includes: a group of lenses configured to collect incident light; a lens supporting member including a fitting portion into which the group of lenses is fitted; a prism configured to reflect light collected by the group of lenses; and an image sensor having a light receiving unit configured to receive the light reflected by the prism and to perform a photoelectric conversion on the received light to generate an electric signal. The lens supporting member has a cutout or an opening portion into which the prism is fitted. The lens supporting member is connected to a surface of the image sensor where the prism is mounted.

4 Claims, 8 Drawing Sheets (51) Int. Cl.
*A61B 1/00* (2006.01)
*G02B 5/04* (2006.01)
*G02B 23/02* (2006.01)
*H04N 5/225* (2006.01)
*H04N 5/335* (2011.01)
*G02B 7/00* (2006.01)
*G02B 13/00* (2006.01)

(52) U.S. Cl.
CPC .......... *A61B 1/00163* (2013.01); *A61B 1/051* (2013.01); *G02B 5/04* (2013.01); *G02B 23/02* (2013.01); *G02B 23/243* (2013.01); *H04N 5/2254* (2013.01); *H04N 5/2256* (2013.01); *H04N 5/335* (2013.01); *G02B 7/003* (2013.01); *G02B 13/0065* (2013.01); *H04N 2005/2255* (2013.01)

(58) Field of Classification Search
CPC .. G02B 23/243; G02B 23/2484; G02B 23/02; G02B 7/1805; G02B 13/0065; H04N 5/2254; H04N 2005/2255
See application file for complete search history.

(56) References Cited

U.S. PATENT DOCUMENTS

| | | | | |
|---|---|---|---|---|
| 4,741,327 A * | 5/1988 | Yabe | .................. | A61B 1/00177 348/65 |
| 4,809,680 A * | 3/1989 | Yabe | ........................ | A61B 1/05 348/65 |
| 4,832,003 A * | 5/1989 | Yabe | ...................... | A61B 1/051 348/65 |
| 6,319,196 B1 * | 11/2001 | Minami | ................... | A61B 1/05 348/76 |
| 2002/0040179 A1 * | 4/2002 | Takahashi | .......... | A61B 1/00096 600/129 |
| 2002/0057344 A1 * | 5/2002 | Miyake | ................ | H04N 5/2254 348/207.99 |
| 2005/0182299 A1 * | 8/2005 | D'Amelio | .......... | A61B 1/00096 600/175 |
| 2008/0088701 A1 * | 4/2008 | Unsai | .................. | A61B 1/00096 348/65 |
| 2009/0076331 A1 | 3/2009 | Konwitz et al. | | |
| 2012/0293641 A1 * | 11/2012 | Nagamizu | .......... | A61B 1/00163 348/65 |
| 2013/0120647 A1 | 5/2013 | Negishi | | |
| 2013/0314521 A1 * | 11/2013 | Satake | ............... | A61B 1/00096 348/76 |
| 2014/0078280 A1 * | 3/2014 | Yoshida | ............. | A61B 1/00163 348/76 |
| 2015/0272430 A1 * | 10/2015 | Oishi | ................. | A61B 1/00128 600/112 |

FOREIGN PATENT DOCUMENTS

| | | |
|---|---|---|
| JP | 2002-045333 A | 2/2002 |
| JP | 2011-237525 A | 11/2011 |
| WO | 2012/169444 A1 | 12/2012 |

OTHER PUBLICATIONS

International Search Report dated May 12, 2015 issued in PCT/JP2015/054152.

* cited by examiner

IMAGING DEVICE FOR IMAGING INSIDE OF SUBJECT AND ENDOSCOPE DEVICE USING THE SAME

CROSS REFERENCES TO RELATED APPLICATIONS

This application is a continuation of PCT international application Ser. No. PCT/JP2015/054152, filed on Feb. 16, 2015 which designates the United States, incorporated herein by reference, and which claims the benefit of priority from Japanese Patent Application No. 2014-040992, filed on Mar. 3, 2014, incorporated herein by reference.

BACKGROUND

1. Technical Field

The disclosure relates to an imaging device provided at a distal end of an insertion portion of an endoscope that is configured to be inserted into a subject to image an inside of the subject. The disclosure also relates to an endoscope device using the imaging device.

2. Related Art

Conventionally, endoscope devices have been widely used for various examinations in a medical field and an industrial field. Among them, endoscope devices for medical use can perform observation or the like of a subject site by inserting, into a subject such as a patient, an elongated flexible insertion portion having a distal end portion in which an imaging device has been incorporated. In consideration of easiness of insertion into the subject, the insertion portion needs to be thinned in diameter.

Generally, an imaging device that is used in an endoscope or the like is configured such that an outer peripheral portion of a group of lenses as an objective optical system is fixed by a lens barrel made of metal, and the lens barrel is held by a tubular lens barrel holding member, whereby positions in a radial direction and an optical axis direction of the group of lenses are defined. As a technique for thinning a diameter of the insertion portion, such an endoscope imaging device has been disclosed that an interval in an optical path direction is provided in a lens barrel holding member that holds a lens barrel of an objective optical system, and an outer peripheral surface of this interval portion is cut and arranged close to an upper surface side of a solid state image sensor, whereby a height dimension of the endoscope imaging device is reduced (for example, refer to JP 2000-271066 A and JP 2002-45333 A).

SUMMARY

In some embodiments, an imaging device includes: a group of lenses configured to collect incident light; a lens supporting member including a fitting portion into which the group of lenses is fitted; a prism configured to reflect light collected by the group of lenses; and an image sensor having a light receiving unit configured to receive the light reflected by the prism and to perform a photoelectric conversion on the received light to generate an electric signal. The lens supporting member has a cutout or an opening portion into which the prism is fitted. The lens supporting member is connected to a surface of the image sensor where the prism is mounted.

In some embodiments, an endoscope device includes the imaging device that is configured to be inserted into a living body to image an inside of the living body.

The above and other features, advantages and technical and industrial significance of this invention will be better understood by reading the following detailed description of presently preferred embodiments of the invention, when considered in connection with the accompanying drawings.

DETAILED DESCRIPTION

Reference will be made below to an endoscope device having an imaging module as modes for carrying out the present invention (hereinafter referred to as "embodiment(s)"). The present invention is not limited by the embodiment. The same reference signs are used to designate the same elements throughout the drawings. Note that the drawings are only schematic, and a relation between thickness and width of each member and a ratio of each member or the like are different from actual ones. Dimensions and ratios in the different drawings may also be different from one another.

First Embodiment

Figure 1:
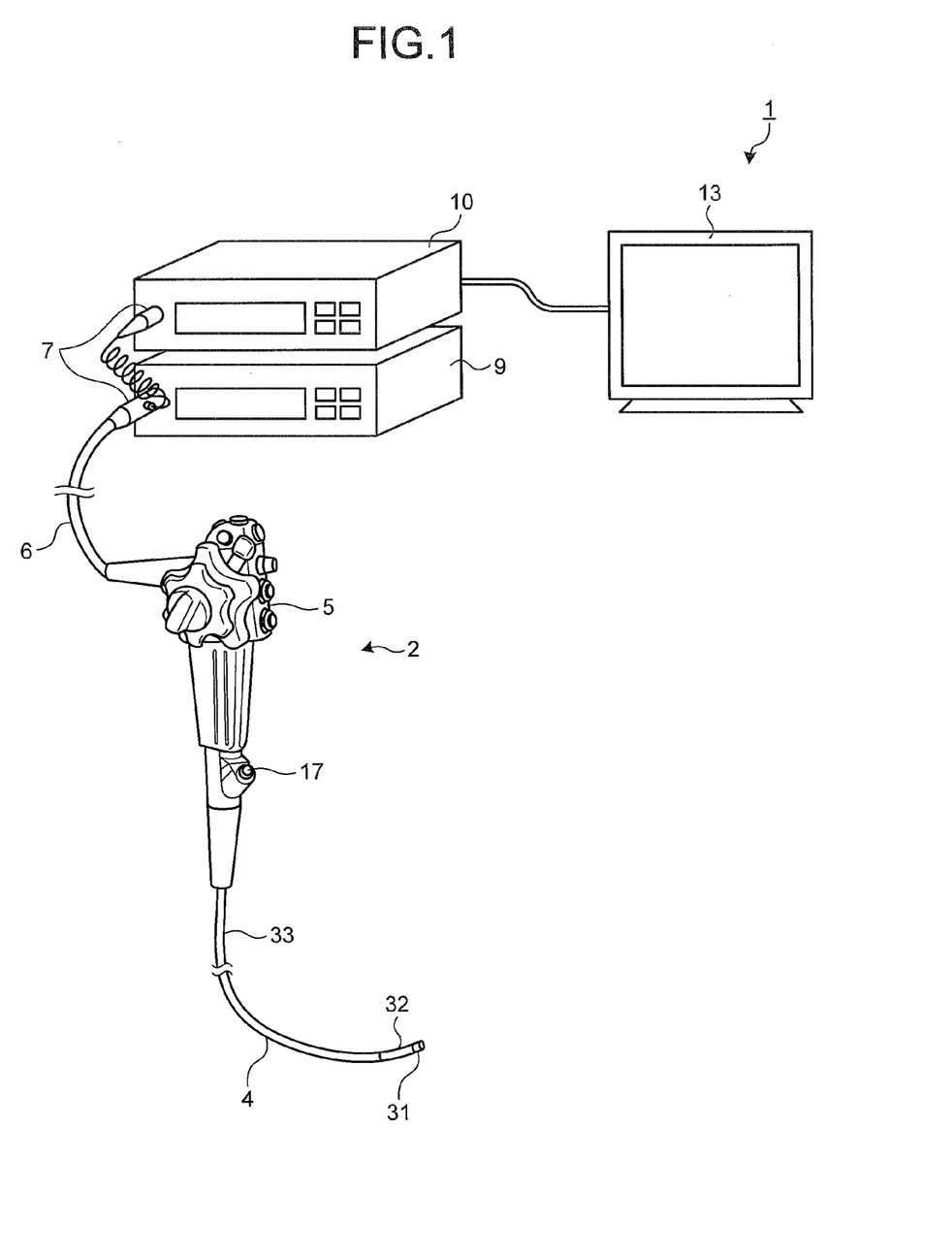
FIG. 1 is a schematic view of an overall configuration of an endoscope device according to a first embodiment.

FIG. 1 is a schematic view of an overall configuration of an endoscope system according to the embodiment of the present invention. As illustrated in FIG. 1, an endoscope device 1 includes an endoscope 2, a universal code 6, a connector 7, a light source device 9, a processor (control device) 10, and a display device 13.

The endoscope 2 captures an in-vivo image of a subject and outputs an imaging signal by inserting an insertion portion 4 into the subject. An electric cable bundle within the universal code 6 is extended to a distal end of the insertion portion 4 of the endoscope 2 and connected to an imaging device provided at a distal end portion 31 of the insertion portion 4.

The connector 7 is provided at a proximal end of the universal code 6, connected to the light source device 9 and the processor 10, performs a predetermined signal process on an imaging signal output from the imaging device at the distal end portion 31 connected to the universal code 6, and performs an analog-digital conversion (A/D conversion) on the imaging signal to output the signal as an image signal.

The light source device 9 is configured by using, for example, a white LED. Pulsed white light emitted by the light source device 9 passes through the connector 7 and the universal code 6 to become illumination light to irradiate an object from the distal end of the insertion portion 4 of the endoscope 2.

The processor 10 performs a predetermined image process on the image signal output from the connector 7, and controls the entire endoscope device 1. The display device 13 displays the image signal processed by the processor 10.

An operating unit 5 is connected to a proximal end side of the insertion portion 4 of the endoscope 2. Various buttons and knobs or the like for operating an endoscope function are provided on the operating unit 5. A treatment tool insertion opening 17 is provided in the operating unit 5. A treatment tool such as living body forceps, an electric scalpel, and an examination probe is inserted into a subject through the treatment tool insertion opening 17.

The insertion portion 4 includes the distal end portion 31, a bendable portion 32, and a flexible tube portion 33. The imaging device is provided at the distal end portion 31. The bendable portion 32 is continuously provided at a proximal end side of the distal end portion 31 and bendable in a plurality of directions. The flexible tube portion 33 is continuously provided at a proximal end side of the bendable portion 32. A bending tube provided within the bendable portion 32 is bent by an operation for a bending operation knob provided on the operating unit 5, and bendable, for example, in four directions including upward, downward, left, and right directions as a bending wire inserted into the insertion portion 4 is pulled or loosened.

A light guide (not illustrated) that delivers illumination light from the light source device 9 is arranged in the endoscope 2. An illumination lens (not illustrated) is arranged at an emission end of the illumination light delivered through the light guide. The illumination lens is provided at the distal end portion 31 of the insertion portion 4, and the illumination light is radiated toward a subject.

Figure 2:
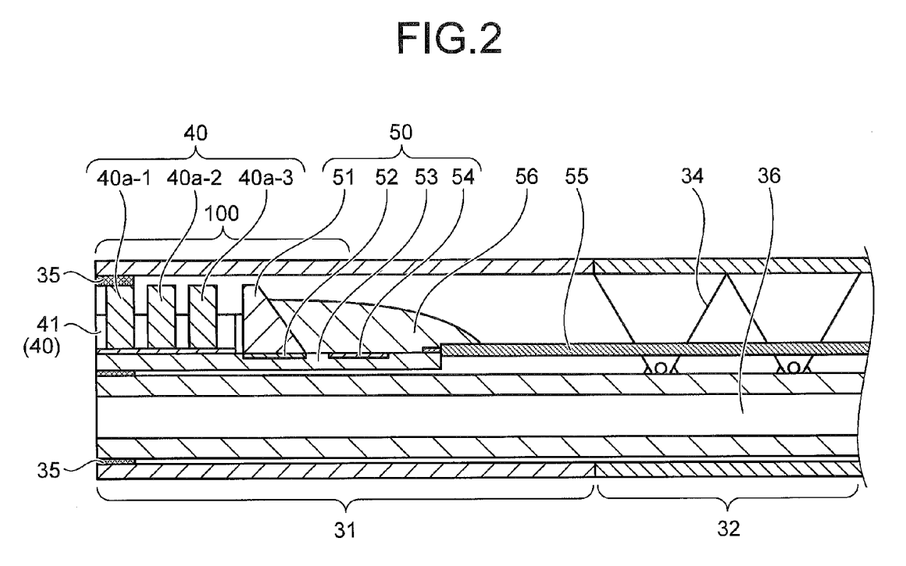
FIG. 2 is a partial cross-sectional view of a distal end of an endoscope illustrated in FIG. 1.

Next, a configuration of the distal end portion 31 of the endoscope 2 will be described in detail. FIG. 2 is a partial cross-sectional view of a distal end of the endoscope 2. FIG. 2 is the cross-sectional view cut off by such a plane as to be orthogonal to a substrate surface of the imaging device provided at the distal end portion 31 of the endoscope 2, as to be parallel to an optical axis direction of incident light for the imaging device, and as to include a vertical axis. In FIG. 2, the distal end portion 31 of the insertion portion 4 of the endoscope 2 and a part of the bendable portion 32 are illustrated.

As illustrated in FIG. 2, the bendable portion 32 is bendable in the four directions including the upward, downward, left, and right directions as the bending wire inserted into the bending tube 34 is pulled or loosened. An imaging device 100 is provided at an upper part of the inside of the distal end portion 31 provided to extend from a distal end side of the bendable portion 32. At a lower part, a treatment tool channel 36 through which various treatment tools are extended is formed.

The imaging device 100 has a lens unit 40 and an imaging unit 50 arranged at a proximal end side of the lens unit 40. The imaging device 100 is bonded to the inside of the distal end portion 31 by an adhesive agent. The distal end portion 31 is formed of a rigid member for forming an internal space in which the imaging device 100 is housed. An outer peripheral portion of a proximal end of the distal end portion 31 is covered with a pliable covering pipe (not illustrated). A member on a proximal end side of the distal end portion 31 is made of a flexible member such that the bendable portion 32 can be bent.

The lens unit 40 has a plurality of objective lenses 40$a$-1 to 40$a$-3 and a lens supporting member 41 that supports the objective lenses 40$a$-1 to 40$a$-3. The lens unit 40 is fixed to the distal end portion 31 when the lens supporting member 41 and an upper end of the objective lens 40$a$-1 are inserted to be fitted and fixed to a distal end fixing portion 35 within the distal end portion 31.

The imaging unit 50 includes a prism 51 and an image sensor 53. The prism 51 reflects light output through the objective lenses 40$a$-1 to 40$a$-3 of the lens unit 40. The image sensor 53 has a light receiving unit 52 that receives the light reflected by the prism 51 and performs a photoelectric conversion on the received light to generate an electric signal. The image sensor 53 is transversely set so that the light receiving unit 52 is arranged horizontally. The prism 51 is bonded on the light receiving unit 52. A distal end of each signal cable 55 of the electric cable bundle is connected to a proximal end of the image sensor 53. A substrate may be connected to the image sensor 53, and an electronic component constituting a processing circuit 54 and the signal cable 55 may be mounted on or connected to the substrate.

A proximal end of each signal cable 55 extends in a proximal end direction of the insertion portion 4. The electric cable bundle is arranged to be inserted into the insertion portion 4, and provided to extend to the connector 7 through the operating unit 5 and the universal code 6 illustrated in FIG. 1.

Light that has come from one end of the lens supporting member 41 is collected by the objective lenses 40$a$-1 to 40$a$-3 to enter the prism 51. The light receiving unit 52 selected from among a CCD image sensor, a CMOS image sensor or the like is formed at a position where the light receiving unit 52 can receive the light radiated from the prism 51. The light receiving unit 52 converts the received light to an imaging signal. The imaging signal passes through the signal cable 55 connected to the image sensor 53 and the connector 7, and is output to the processor 10. In the description of the present application, a side of the lens supporting member 41 from which light comes, that is, a side on which the objective lenses 40$a$-1 to 40$a$-3 are arranged, is referred to as a front end portion, and a side of the lens supporting member 41 on which the prism 51 is arranged is referred to as a rear end portion.

The lens supporting member 41 is bonded to the image sensor 53 by an adhesive agent. A rear end of the lens supporting member 41 and a rear end side of an assembling position of the prism 51 on the image sensor 53 are sealed by a sealing resin 56.

Figure 3A:
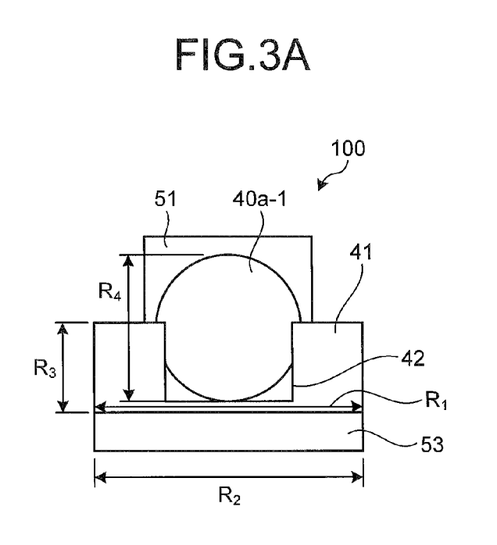
FIG. 3A is a front view of an imaging device.
Figure 3B:
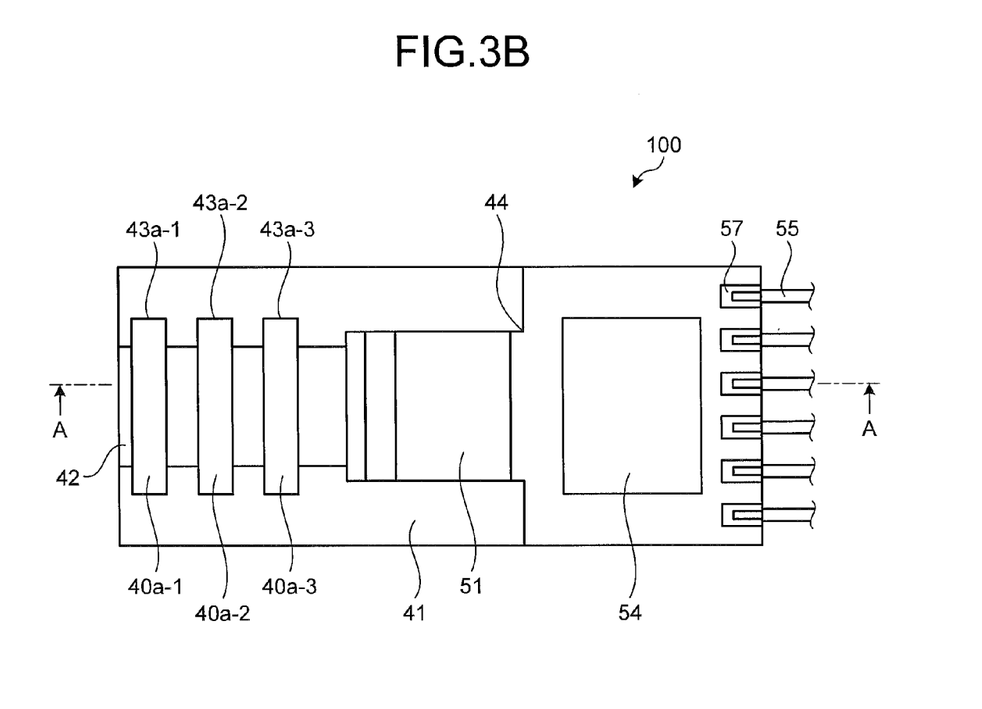
FIG. 3B is a top view of the imaging device.
Figure 3C:
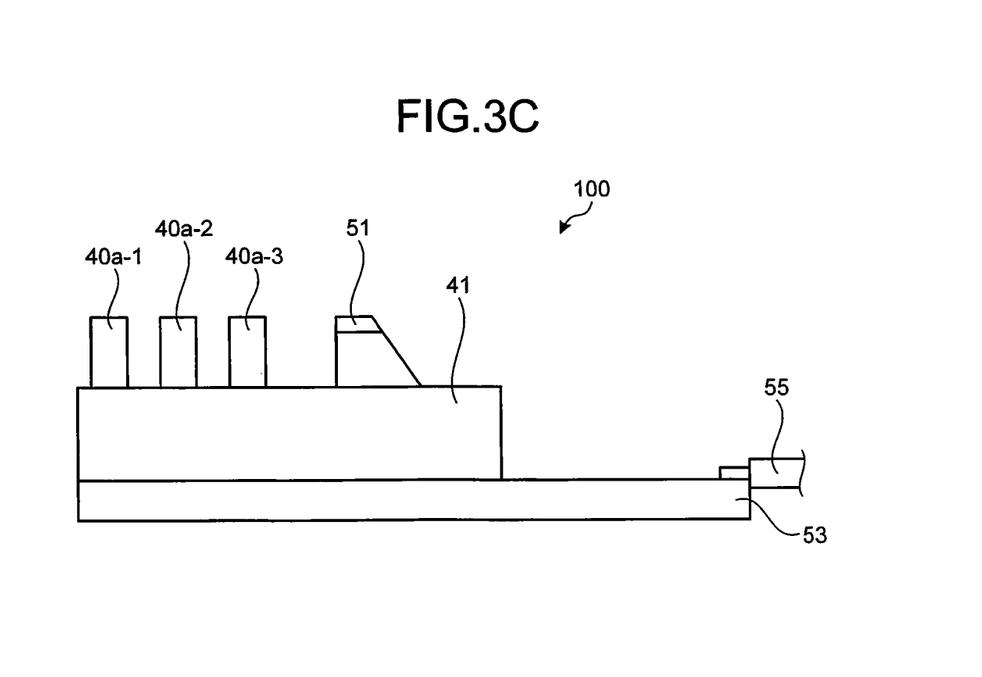
FIG. 3C is a side view of the imaging device.
Figure 3D:
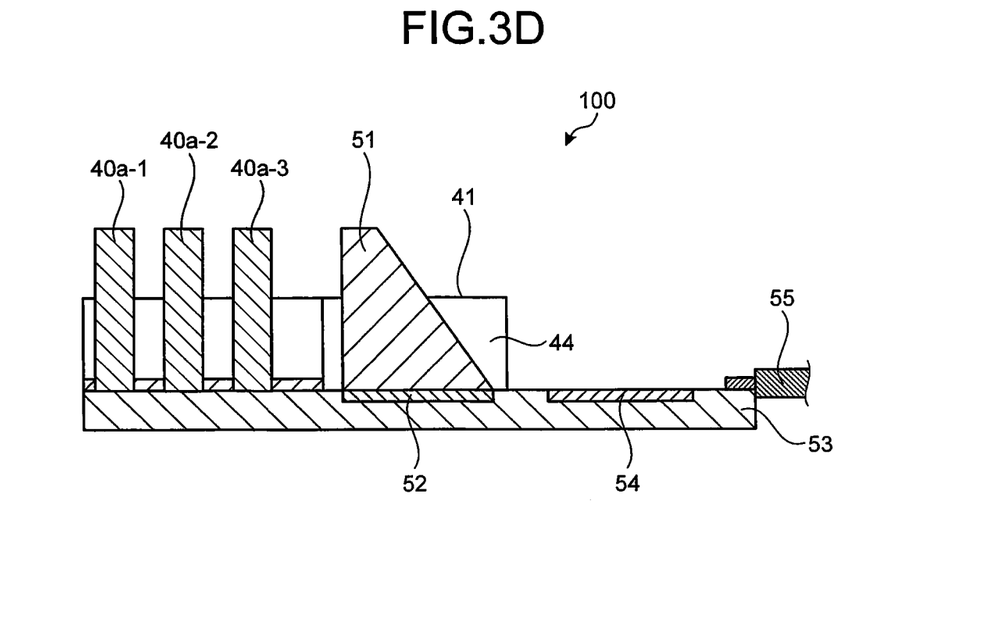
FIG. 3D is a cross-sectional view taken along line A-A of FIG. 3B.

Next, the imaging device 100 will be described. FIG. 3A is a front view of the imaging device 100. FIG. 3B is a top view of the imaging device 100. FIG. 3C is a side view of the imaging device 100. FIG. 3D is a cross-sectional view taken along line A-A of FIG. 3B.

As illustrated in FIGS. 3A to 3D, the lens supporting member 41 has a plate shape in which a groove portion 42, fitting portions 43$a$-1 to 43$a$-3, and a cutout 44 are formed. The groove portion 42 serves as an optical path of incident light. The objective lenses 40$a$-1 to 40$a$-3 are fitted into the fitting portions 43$a$-1 to 43$a$-3. The prism 51 can be fitted into the cutout 44.

The fitting portions 43*a*-1 to 43*a*-3 only need to be configured to fix the objective lenses 40*a*-1 to 40*a*-3 and be capable of holding intervals therebetween. In the first embodiment, the fitting portions 43*a*-1 to 43*a*-3 are formed in side surfaces of the groove portion 42 that face each other. However, a bottom surface of the groove portion 42 may also be cut to form a fitting portion. By forming the fitting portion on the bottom surface of the groove portion 42, the small-sized distal end portion 31 can be achieved. When the bottom surface of the groove portion 42 is cut to form the fitting portion, a through hole may be formed such that the objective lenses 40*a*-1 to 40*a*-3 come into contact with the image sensor 53. Alternatively, a width of the groove portion 42 may be made the same as a diameter of each of the objective lenses 40*a*-1 to 40*a*-3, whereby the fitting portions 43*a*-1 to 43*a*-3 may be formed only in the bottom surface of the groove portion 42.

The cutout 44 is formed on a rear end side of the lens supporting member 41 to cause the prism 51 to be fitted into the cutout 44. A side surface of the cutout 44 parallel to the optical axis direction is formed to have such a length that the side surface of the cutout 44 parallel to the optical axis direction has contact with a side surface of the prism 51 parallel to the optical axis direction. Since the side surface of the cutout 44 parallel to the optical axis direction is formed to have contact with a part of the side surface of the prism 51 parallel to the optical axis direction, a focus adjustment can be easily performed. In the first embodiment, the cutout 44 is employed as a structure to cause the prism 51 to be fitted. However, an opening portion may be employed such that a rear end of the cutout 44 is closed. When the opening portion is employed, a side surface of the opening portion that is parallel to the optical axis direction is formed to have contact with a part of the side surface of the prism 51 that is parallel to the optical axis direction, and a length of the side surface of the opening portion that is parallel to the optical axis direction is made longer than a length in the optical axis direction of a mounting surface where the prism 51 is mounted.

In the first embodiment, a width R1 of the lens supporting member 41 is the same length as a width R2 of the image sensor 53. However, the width R1 of the lens supporting member 41 may be made shorter than the width R2 of the image sensor 53 as long as the objective lenses 40*a*-1 to 40*a*-3 can be fixed. A thickness R3 of the lens supporting member 41 is preferably smaller than a diameter R4 of each of the objective lenses 40*a*-1 to 40*a*-3.

The image sensor 53 includes the light receiving unit 52 and the processing circuit 54. A connection electrode 57 that connects the signal cable 55 is also formed on the image sensor 53. The lens supporting member 41 is connected on the surface of the image sensor 53 where the prism 51 is mounted.

Figure 4:
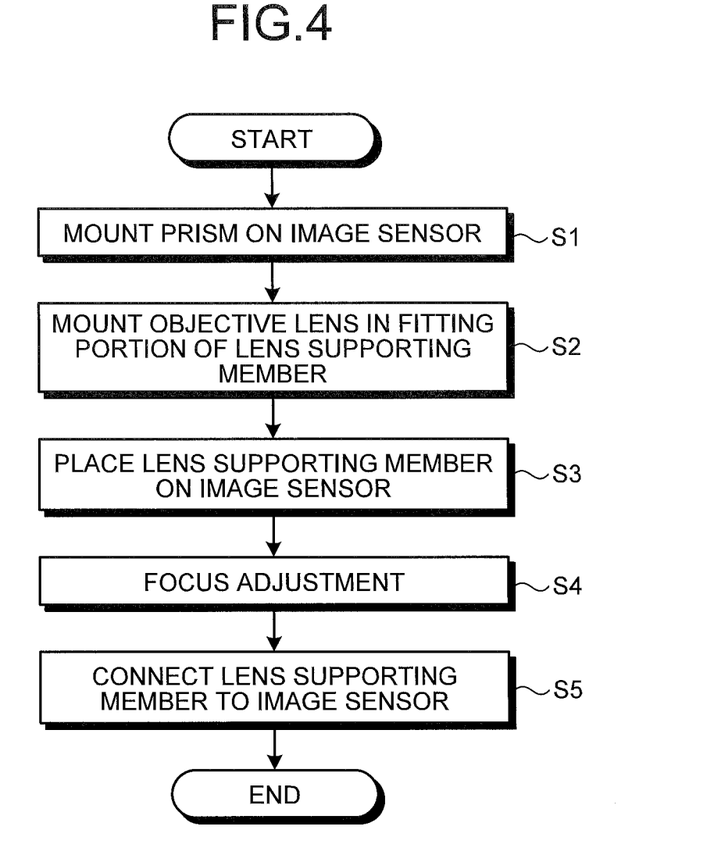
FIG. 4 is a flowchart illustrating a process for manufacturing the imaging device.

Next, a method for manufacturing the imaging device 100 of the first embodiment will be described. FIG. 4 is a flowchart illustrating a process for manufacturing the imaging device 100.

First, the prism 51 is mounted on a surface of the light receiving unit 52 of the image sensor 53 (step S1), and the objective lenses 40*a*-1 to 40*a*-3 are fitted into the fitting portions 43*a*-1 to 43*a*-3 of the lens supporting member 41 and fixed by an adhesive agent (step S2).

The lens supporting member 41 to which the objective lenses 40*a*-1 to 40*a*-3 have been fixed is placed on the image sensor 53 on which the prism 51 has been mounted (step S3). At the time of the placement, the lens supporting member 41 is placed in such a manner that the cutout 44 of the lens supporting member 41 is fitted in the prism 51.

After the lens supporting member 41 is placed on the image sensor 53, the lens supporting member 41 holding the objective lenses 40*a*-1 to 40*a*-3 is moved in the optical axis direction, whereby the focus adjustment is performed (step S4). The focus adjustment is preferably performed by an output image in such a manner that a probe or the like is made to abut on the connection electrode 57 of the signal cable 55.

After a position of the lens supporting member 41 is defined by the focus adjustment, the lens supporting member 41 is bonded and fixed to the image sensor 53 (step S5). The fixation of the lens supporting member 41 and the image sensor 53 only needs to be performed in such a manner that an adhesive agent is applied in advance to a surface of the lens supporting member 41 and/or the image sensor 53, and after the focus adjustment, the adhesive agent is hardened by means of heating, ultraviolet irradiation or the like to finish the bonding.

In the first embodiment, since the objective lenses 40*a*-1 to 40*a*-3 can be held in such a manner that the objective lenses 40*a*-1 to 40*a*-3 are fitted into the fitting portions 43*a*-1 to 43*a*-3 of the lens supporting member 41, the small-sized imaging device 100 can be achieved without the need to use a member having an outer frame that holds the lenses. Since the lens supporting member 41 includes the cutout 44 into which the prism 51 mounted on the image sensor 53 can be fitted, and the lens supporting member 41 is moved in the optical axis direction through the cutout 44, the focus adjustment can be easily performed. Furthermore, since the imaging device 100 according to the first embodiment is configured such that the processing circuit 54 is formed on the image sensor 53, a substrate for mounting an electric component does not need to be used. When the imaging device 100 is used as the endoscope device, the distal end portion 31 can be shortened and a step or the like of connecting the substrate to the image sensor can be omitted.

Second Embodiment

Figure 5A:
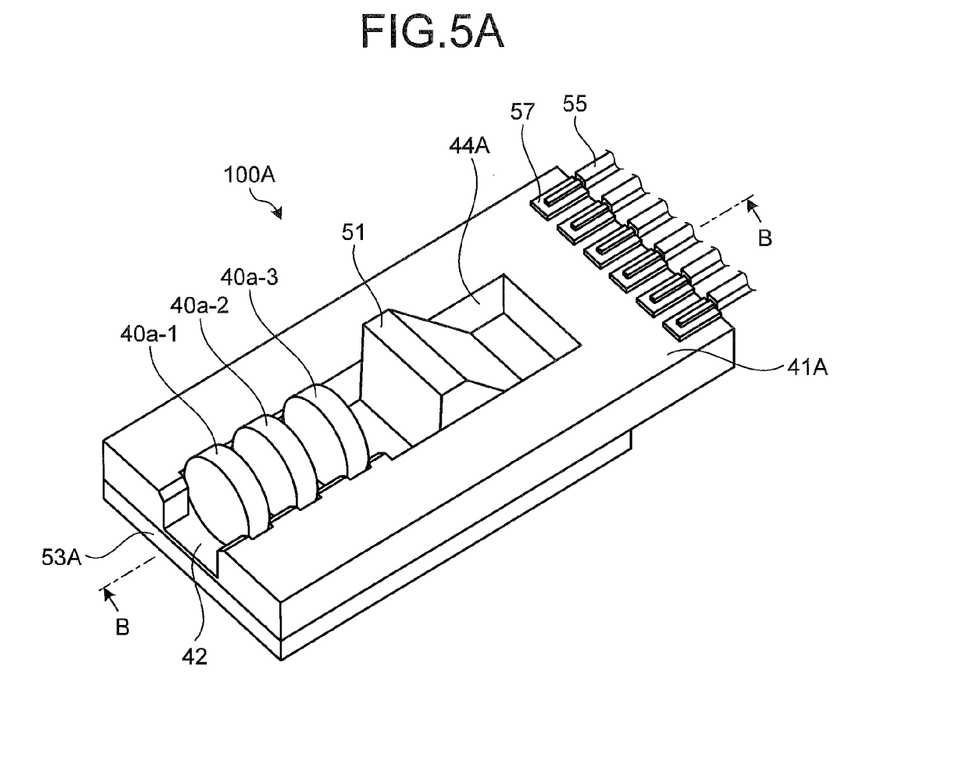
FIG. 5A is a perspective view of an imaging device according to a second embodiment.
Figure 5B:
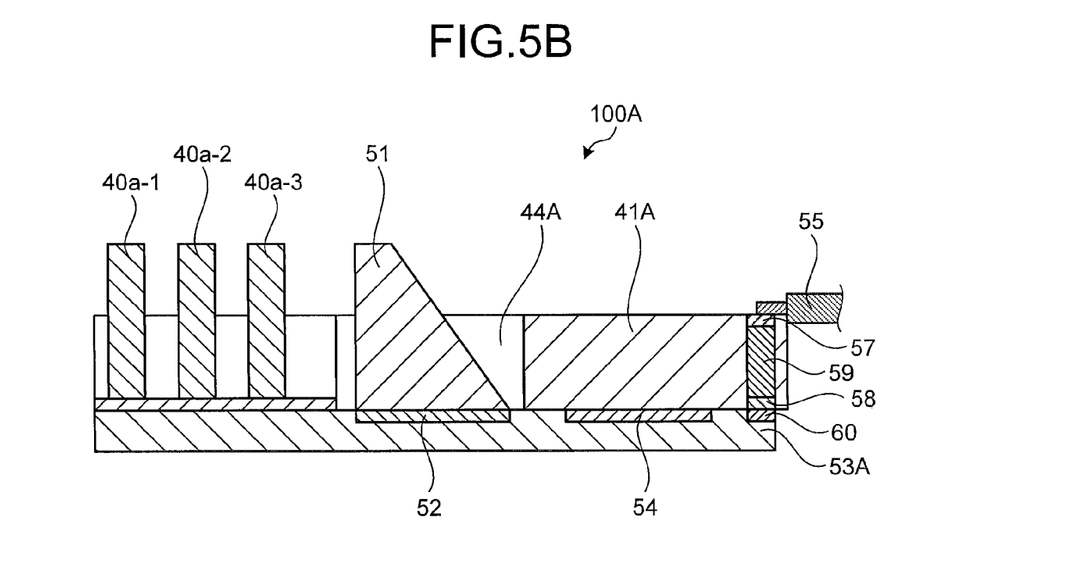
FIG. 5B is a cross-sectional view taken along line B-B of FIG. 5A.

An imaging device according to a second embodiment is different from that of the first embodiment in that a connection electrode of a signal cable 55 is formed on a lens supporting member. FIG. 5A is a perspective view of the imaging device according to the second embodiment. FIG. 5B is a cross-sectional view taken along line B-B of FIG. 5A.

As illustrated in FIGS. 5A and 5B, an opening portion 44A into which a prism 51 can be fitted is formed in a lens supporting member 41A, and the connection electrode 57 that connects the signal cable 55 is formed on a rear end side of the lens supporting member 41A. The connection electrode 57, together with a connection electrode 58 formed on a rear surface and a via 59, forms a through electrode.

A connection electrode 60 is formed on an image sensor 53A together with a light receiving unit 52 and a processing circuit 54, and electrically connected to the connection electrode 58 of the lens supporting member 41A.

Figure 6A:
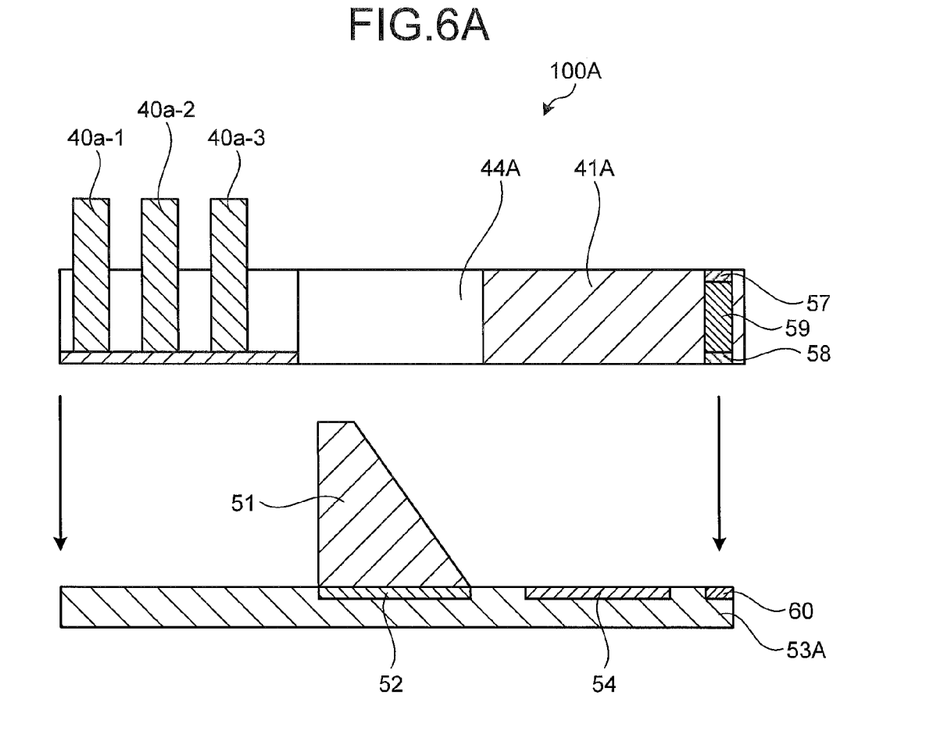
FIGS. 6A and 6B are illustrative views of a process for manufacturing the imaging device according to the second embodiment.
Figure 6B:
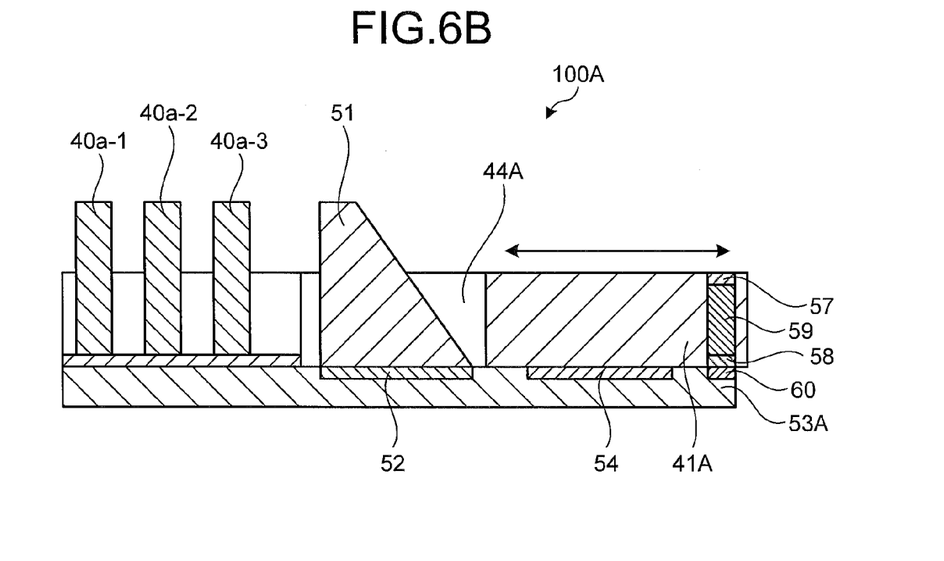

Next, a method for manufacturing an imaging device 100A of the second embodiment will be described. FIGS. 6A and 6B are illustrative views of a process for manufacturing the imaging device 100A.

In the same way as the first embodiment, the prism 51 is mounted on a surface of the light receiving unit 52 of the image sensor 53A, and objective lenses 40*a*-1 to 40*a*-3 are fitted into fitting portions 43*a*-1 to 43*a*-3 of the lens supporting member 41A and fixed by an adhesive agent. As illustrated in FIG. 6A, the lens supporting member 41A to which the objective lenses 40a-1 to 40a-3 have been fixed is placed, through the opening portion 44A, on the image sensor 53A on which the prism 51 has been mounted. At the time of the placement, the lens supporting member 41A is placed in such a manner that the connection electrode 58 of the lens supporting member 41A abuts on the connection electrode 60 of the image sensor 53A.

After the lens supporting member 41A is placed on the image sensor 53A, as illustrated in FIG. 6B, the lens supporting member 41A holding the objective lenses 40a-1 to 40a-3 is moved in an optical axis direction, whereby a focus adjustment is performed. The focus adjustment is preferably performed by an output image in such a manner that a probe or the like is made to abut on the connection electrode 57. The connection electrodes 58 and 60 are preferably designed to each have such a length that the electrical connection can be established even when a position in the optical axis direction is adjusted by the focus adjustment. After the focus adjustment, the lens supporting member 41A is bonded and fixed to the image sensor 53A.

In the second embodiment, in the same way as the first embodiment, since the objective lenses 40a-1 to 40a-3 can be held in such a manner that the objective lenses 40a-1 to 40a-3 are fitted into the fitting portions 43a-1 to 43a-3 of the lens supporting member 41A, the small-sized imaging device 100A can be achieved without the need to use a member having an outer frame that holds the lenses. Since the lens supporting member 41A includes the opening portion 44A into which the prism 51 mounted on the image sensor 53A can be fitted, and the lens supporting member 41A is moved in the optical axis direction through the opening portion 44A, the focus adjustment can be easily performed. Furthermore, since the imaging device 100A according to the second embodiment is configured such that the processing circuit 54 is formed on the image sensor 53A, a substrate for mounting an electric component does not need to be used. When the imaging device 100A is used as the endoscope device, therefore, the distal end portion 31 can be shortened and a step or the like of connecting the substrate to the image sensor can be omitted.

Although the lens supporting member 41A of the second embodiment electrically connects the image sensor 53A to the signal cable 55 by means of the through electrode, the connection electrodes 57 and 58 may be connected by wiring formed on a surface of the lens supporting member 41A. When the connection electrodes 57 and 58 are connected by the wiring, the connection electrodes 57 and 58 only need to be formed on a side surface on a rear end of the lens supporting member 41A.

Figure 7A:
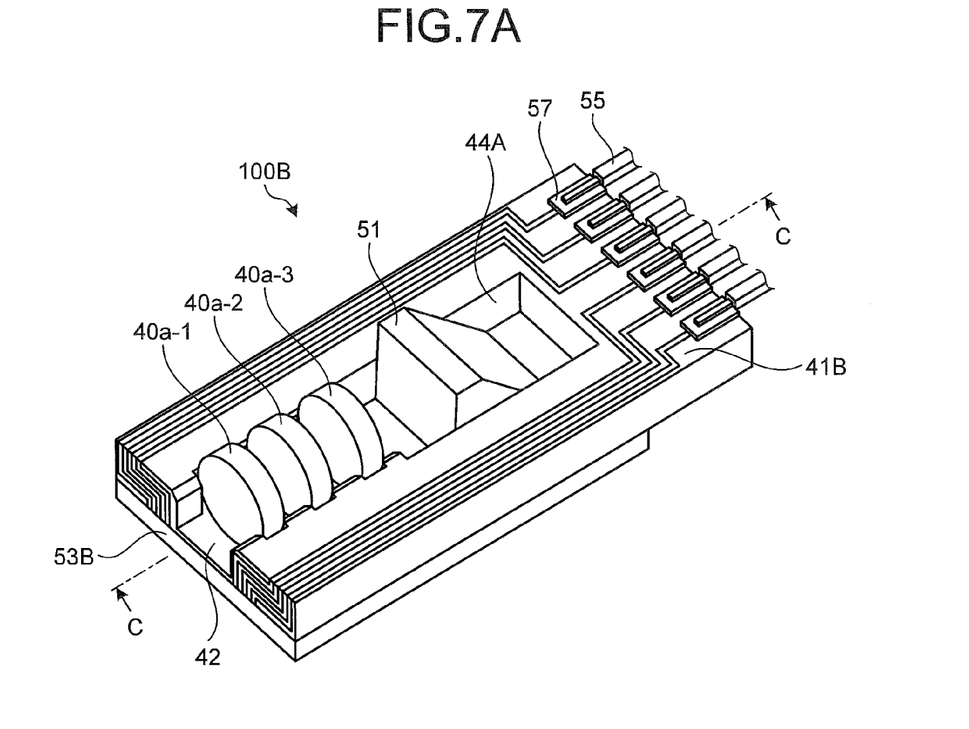
FIG. 7A is a perspective view of an imaging device according to a modification of the second embodiment.
Figure 7B:
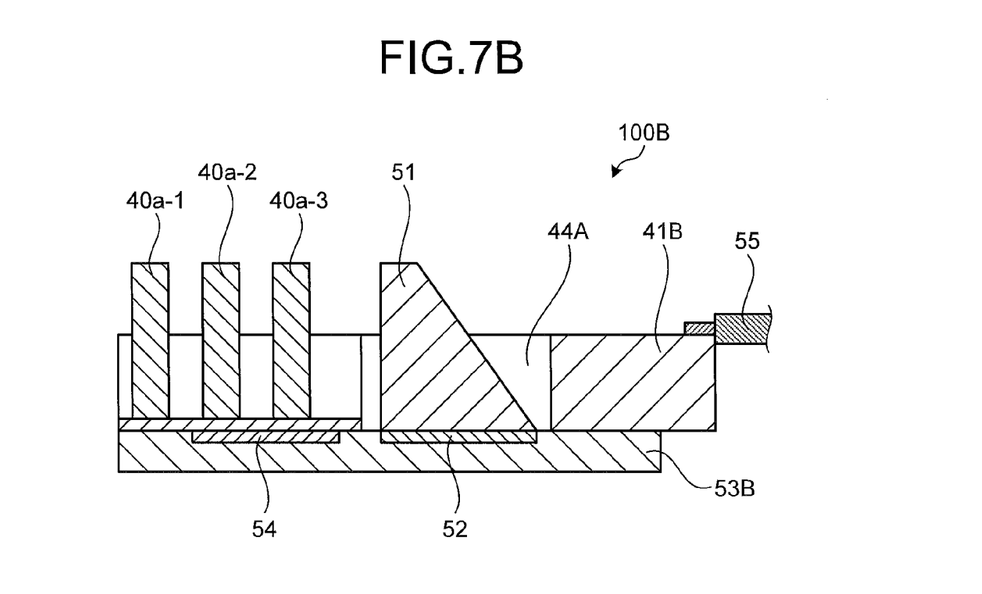
FIG. 7B is a cross-sectional view taken along line C-C of FIG. 7A.

If the processing circuit 54 is formed on a front end portion of the image sensor, that is, below the objective lenses 40a-2 to 40a-3, the small-sized imaging device can be achieved. FIG. 7A is a perspective view of an imaging device according to a modification of the second embodiment. FIG. 7B is a cross-sectional view taken along line C-C of FIG. 7A.

As illustrated in FIGS. 7A and 7B, an imaging device 100B according to the modification is configured such that a processing circuit 54 is formed on a front end portion of an image sensor 53B, and a connection electrode (not illustrated) is formed on a further front end side of the image sensor 53B below an objective lens 40a-1.

On a side close to a surface of a lens supporting member 41B connected to the image sensor 53B, a connection electrode (not illustrated) connected to a connection electrode on a side close to the image sensor 53B is formed. On a surface of the lens supporting member 41B, wiring that couples a connection electrode 57 to which a signal cable 55 is connected to a connection electrode connected to an image sensor electrode of the image sensor 53B is formed.

The imaging device 100B according to the modification exhibits effects in the same way as the second embodiment, and the processing circuit 54 is formed on the front end portion of the image sensor 53B. When the imaging device 100B is used as the endoscope device, therefore, the distal end portion 31 can be further shortened.

According to some embodiments, a lens supporting member includes a fitting portion into which a group of lenses is fitted to hold the group of lenses. With this structure, it is possible to realize a small-sized imaging device. The lens supporting member further includes a cutout or an opening portion into which a prism mounted on an image sensor can be fitted. Since the lens supporting member can be moved in an optical axis direction through the cutout or the opening portion, a focus adjustment can be easily performed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging device comprising:
    a group of lenses configured to collect incident light;
    a lens supporting member including a groove serving as an optical path of the incident light and a fitting portion having recesses into which individual lenses of the group of lenses are fitted, the recesses being provided within the groove to fix an interval between the individual lenses;
    a prism configured to reflect light collected by the group of lenses; and
    an image sensor having a light receiving unit configured to receive the light reflected by the prism and to perform a photoelectric conversion on the received light to generate an electric signal, wherein
    the lens supporting member has one of a cutout or an opening portion into which the prism is fitted,
    the lens supporting member is mounted on a surface of the image sensor such that an exit surface of the prism corresponds to the light receiving unit of the image sensor, and
    the lens supporting member is configured to support the group of lenses such that the group of lenses comes into contact with the surface of the image sensor.

2. The imaging device according to claim 1, wherein
    a side surface of the cutout or the opening portion that is parallel to an optical axis direction of the group of lenses has contact with a part of a side surface of the prism that is parallel to the optical axis direction, and
    a length of the side surface of the opening portion that is parallel to the optical axis direction is longer than a length in the optical axis direction of the surface of the image sensor where the prism is mounted.

3. The imaging device according to claim 1, wherein the lens supporting member includes a first connection electrode electrically connected to an electrode of the image sensor, and a second connection electrode configured to connect to a signal cable.

4. An endoscope device comprising:
an insertion section configured to be inserted into a living body; and
the imaging device according to claim 1, the imaging device being disposed at a distal end of the insertion section and configured to image an inside of the living body.

\* \* \* \* \*